US008476017B2

(12) United States Patent
Pietrzkowski

(10) Patent No.: US 8,476,017 B2
(45) Date of Patent: *Jul. 2, 2013

(54) MICROVESICLE-BASED COMPOSITIONS AND METHODS

(75) Inventor: Zbigniew Pietrzkowski, Aliso Viejo, CA (US)

(73) Assignee: Proxy Life Sciene Holdings, Inc., Temecula, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/233,987

(22) Filed: Sep. 15, 2011

(65) Prior Publication Data
US 2012/0009578 A1    Jan. 12, 2012

Related U.S. Application Data

(63) Continuation of application No. 12/488,110, filed on Jun. 19, 2009, now Pat. No. 8,021,847, which is a continuation-in-part of application No. 11/569,757, filed as application No. PCT/US2005/010674 on Mar. 30, 2005.

(60) Provisional application No. 61/074,218, filed on Jun. 20, 2008, provisional application No. 60/576,395, filed on Jun. 2, 2004.

(51) Int. Cl.
*C12Q 1/68* (2006.01)

(52) U.S. Cl.
USPC .......................................................... 435/6.1

(58) Field of Classification Search
None
See application file for complete search history.

(56) References Cited

U.S. PATENT DOCUMENTS

| | | | |
|---|---|---|---|
| 5,165,938 A | 11/1992 | Knighton | |
| 5,428,008 A | 6/1995 | Chao et al. | |
| 6,812,023 B1 | 11/2004 | Lamparski et al. | |
| 6,899,863 B1 | 5/2005 | Dhellin et al. | |
| 6,916,634 B2 | 7/2005 | Kopreski | |
| 7,198,923 B1 | 4/2007 | Abrignani et al. | |
| 7,897,356 B2 | 3/2011 | Klass et al. | |
| 2002/0106684 A1 | 8/2002 | Kopreski | |
| 2003/0036077 A1 | 2/2003 | Chenchik et al. | |
| 2003/0068642 A1 | 4/2003 | Urnovitz | |
| 2004/0028692 A1 | 2/2004 | Zitvogel | |
| 2004/0082511 A1 | 4/2004 | Watzek | |
| 2010/0113290 A1 | 5/2010 | Klass et al. | |
| 2010/0151480 A1 | 6/2010 | Taylor et al. | |
| 2010/0184046 A1 | 7/2010 | Klass et al. | |
| 2010/0196426 A1 | 8/2010 | Skog et al. | |
| 2010/0203529 A1 | 8/2010 | Klass et al. | |
| 2011/0053157 A1 | 3/2011 | Skog et al. | |

FOREIGN PATENT DOCUMENTS

| | | |
|---|---|---|
| WO | 90/10872 | 9/1990 |
| WO | 01/36601 | 5/2001 |
| WO | 2005/121369 | 12/2005 |

OTHER PUBLICATIONS

Microvesicles are a Source of Contaminating Cellular Proteins Found in Purified HIV-1 Preparations (Virology 1997); Mar. 31; 230(1):134-144.
Basyuk E. Galli et al, Retroviral genomic RNA's are transported to the plasma membrane by endosomal vesicles—5(1):161-74, Developmental Cell. 2003.
Thery, C., Boussac, Proteomic Analysis of Dendritic Cell-Derived Exosomes: A Secreted Subcellular Compartment Distinct from Apoptotic Vesicles—166(12):7309-18, J. Immunology 2001.
Stinton LM, Eystathioy, Autoantibodies to protein transport and messenger RNA processing pathways: endosomes, lysosomes, Golgi complex, proteasomes, assemblyosomes, exosomes, and GW bodies—110(1)30-44, Clin. Immunol. 2004.
Denzer K. Kleijmeer, Exosome: from internal vesicle of the multivesicular body to intercellular signaling device—113 Pt 19:3365-74. Review, J. Cell Science 2000.
Goset R. Kanjanahaluethai, RNA Replication of Mouse Hepatitis Virus Take Place at Double-Membrane Vesicles Vo. 76 No. 8—76(8): 3697-708, J. Virol. 2002.
J. Cell Biol. Aug. 4, 2003, Hrs regulates multivescular body formation via ESCRT recruitment to endosomes—162(3): 435-42, Bache, K. et al. 2003.
Andre F. Chapnut et al. "Exosomes as potent cell-free peptide-based Vaccine", The Journal of Immunology, vol. 172, No. 4, pp. 2126-2136, 2004.
Hu Q. Shew CR Bally et al. Programmable fusogenic vesicles from intracellular delivery of antisense oligodeoxynucleotides: enhanced cellular uptake and biological effects—1514(1): 1-13, Biochimica Biophysica 2001.
Janowska-Weizorek., A., et al, "Platelet-dervied microparticles bind to hematopoietic stem/progenitor cells and enhance their engraftment", Nov. 15, 2001, vol. 98 No. 10 pp. 3142-3149, Blood.
El-Hefnawy, T., et al., "Characterization of Amplifiable, Circulating RNA in Plasma and Its Potential as a Tool for Cancer Diagnostics", Clinical Chemistry, 2004, vol. 50, No. 3, pp. 564-573.
Andre, F. et al., "Exosmes for cancer immunotherapy", Annals of Oncology, 2004, vol. 15, No. 4, pp. 141-144.
Bazanova, N.V., et al., "Can the presence of an RNA-lipoprotein complex in human blood serum give evidence of a cancerous disease?", Eksp Onckol., 1989, vol. 11, No. 2, pp. 37-39.
Jaroskaw, B. et al., "Circulating tumour-derived microvesicles in plasma of gastric cancer patients", Cancer Immunol Immunother, 2010, vol. 59, No. 6, pp. 841-850.
Camussi, G., et al., "Exosome/microvesicle-mediated epigenetic reprogramming of cells", American Journal of Cancer Research, 2011, vol. 1, No. 1, 2011.
Ceccarini, M., et al., "Biochemical and NMR studies on structure and release conditions of RNA-containing vesicles shed by human colon adenocarcinoma cells", Int. J. Cancer, 1989, vol. 44, pp. 714-721.

(Continued)

*Primary Examiner* — Kenneth R. Horlick
*Assistant Examiner* — David Thomas
(74) *Attorney, Agent, or Firm* — Fish & Associates, PC

(57) ABSTRACT

Methods and compositions for diagnosis and/or analysis of a condition in a mammal are disclosed in which RNA from microvesicles is enriched and differentiated to so obtain a result that is indicative of the condition of tissue or organ from which the microvesicle originated. In especially preferred embodiments, the condition is a neoplastic disease of a human and can be identified and staged by differential analysis of one or more distinct RNAs, optionally together with identification and analysis of a non-RNA component of the microvesicle.

13 Claims, 3 Drawing Sheets

OTHER PUBLICATIONS

Chen, X.Q., et al., "Telomerase RNA as a detection marker in the serum of breast cancer patients", Clinical Cancer Research, 2000, vol. 6, pp. 3823-3826.
International Workshop on Exosomes (IWE), Jan. 19-22, 2011 at Paris France, Program.
Janowska-Wieczorek, A., et al., Proc. Amer. Assoc. Cancer Res. 2004, 45 (abstract).
Johnstone, R. M., et al., "Vesicle formation during reticulocyte maturation", Journal of Biological Chemistry, 1987, vol. 262, No. 19, pp. 9412-9420.
Kuslich, C., et al., American Society of Clinical Oncology Conference, 2010 (poster).
Mathivanan, S., et al., "ExoCarta: A compendium of exosomal proteins and RNA", Proteomics, 2009, vol. 9, 4997-5000.
Miura, N., et al., "Sensitive detection of human telomerase reverse transcriptase mRNA in the serum of patients with hepatocellular carcinoma", Oncology, 2003, vol. 64, pp. 430-434.
Rabinowits, G., et al., "Exosomal microRNA: A diagnostic marker for lung cancer", 2009, vol. 10, No. 1, pp. 42-46.
Ratajczak, J. et al., "Embryonic stem cell-derived microvesicles reprogram hematopoietic progenitors: evidence for horizontal transfer of mRNA and protein delivery", Leukemia, 2006, vol. 20, 847-856.
Ratajczak, J. et al, "Membrane-derived microvesicles: important and underappreciated mediators of cell-to-cell communication", Leukemia, 2006, vol. 20, 14871495.
Silva, J.M., et al., "Detection of epithelial messenger RNA in the plasma of breast cancer patients is associated with poor prognosis tumor characteristics", Clinical Cancer Research, 2001, vol. 7, pp. 2821-2825.
Skog, J. et al., "Glioblastoma microvesicle transport RNA and proteins that promote tumour growth and provide diagnostic biomarkers" Natural Cellular Biology, 2008, vol. 10, No. 2, 1470-1476.
Slomovic, S., et al., "Poluadenylation of ribosomal RNA in human cells", Nucleic Acids Research, 2006, vol. 34, No. 10, 1966-1975.
Taylor, D.D., et al., "MicroRNA signatures of tumor-derived exosomes as diagnostic biomarkers of ovarian cancer", Gynecologic Oncology, 2008, vol. 110, pp. 13-21.
Wieczorek, A.J., et al, "Isolation and characterization of an RNA-preolipid complex associated with the malignant state in humans", Proc. Natl. Acad. Sci. USA, 1985, vol. 82, pp. 3455-3459.
Wieczorek, A.J., et al, "Diagnostic and prognostic value of RNA-proteolipid in sera of patients with malignant disorders following therapy: First clinical evaluation of a novel tumor marker", Cancer Research, 1987, vol. 47, pp. 6407-6412.
Ziegler, A., et al., "Circulating DNA: a new diagnostic gold mine?", Cancer Treat. Rev., 2002, vol. 25, No. 5, pp. 255-271.
Caris Life Science, Carisome Prostate Cancer Assay, Web page http:www.carislifescience.com/future-possibilities-prostate-cancer, 2011.
Shedden, K., et al., "Expluion of Small Molecules in Vesicles Shed by Cancer Cells . . . " Advances in Brief, Cancer Research, Aug. 1, 2003, vol. 63, pp. 4331-4337.
Wacholder, S., et al., "Assessing the Probability That a Positive Report is False . . . " Journal of the National Cancer Institute, Mar. 17, 2004, vol. 96, No. 6.
Kopreski, M.S., et al., "Detection of Tumor Messenger RNA in the Serum of Patients with Malignant Melanoma" Clinical Cancer Research, Aug. 1999, vol. 5, pp. 1961-1965.
Lucentini, J., "Gene Association Studies Typically Wrong", The Scientist: Gene Associates, www.the-scientist.com/article/printe/15157/, vol. 18, No. 24, p. 20, 2004.
Greenbaum, D., et al., "Comparing protein abundance and mRNA expression levels on a genomic scale" Genome Biology, Aug. 29, 2003, vol. 4, No. 117.
Carr, J.M., et al., "Circulating Membrane Vesicles in Leukemic Blood" Cancer Research, Nov. 1985, vol. 45.
Ioannidis, J.P.A., et al., "Replication validity of genetic association studies", Nature genetics, Nov. 2001, vol. 29.
Google Scholar "membrane microparticles OR membrane . . . " Jan. 31, 2009.
Business Wire: First Look at Genome Operating System Revealed at Centennial Celebration; Living.. Jan. 27, 2009.
Dolo, V., et al., "Membrane vesicles shed into the extracellular medium by human breast . . . " Clinical & Experimental Metastasis, vol. 13, No. 4, pp. 277-286, 1995.
Vlassov, V.V., "Extracellular nucleic acids", BioEssays, vol. 39, pp. 654-667, Wiley Periodicals, Inc., 2007.
Heijnen, H.F.G., "Activated Platelets Release Two Types of Membranes . . . ", Blood, Dec. 1, 1999, vol. 94, No. 11, pp. 3791-3799.
Fleischhacker, M. "Biology of circulating mRNA still more questions..", New York Academy of Sciences, 2006.
Rykova, E.Y., et al., "Concentrations of circulating RNA form Healthy Donors . . . " New York Academy of Sciences, 2006.
Wong, B.C.K., et al., "Plasma RNA Integrity Analysis Methodology and Validation" New York Academy of Sciences, 2006.
Janas, T., et al., "RNA visualization of membrane RNAs", RNA Journal, 2003, pp. 1353-1361.
Aizaki, H., et al., "Critical Role of Virion-Associated Cholesterol and . . . " Journal of Virology, Jun. 2008, pp. 5715-5724.
Huang, H., et al., "Hepatitis C virus production by human hepatocytes dependent on assembly and secretion . . . " PNAS, 3 Apr. 3, 2007, vol. 104, No. 14, p. 5848-5853.
Biggiogera, M., et al., "Nuclear RNA is extruded from Apoptotic cells" The Journal of Histochemistry & Cytochemistry, 1998, vol. 46, No. 9, pp. 999-1005.
Ratajczak, M.Z., "Microvesicles: from dust to crown", Blood, Nov. 1, 2006, vol. 108, No. 9.
Janas, T., et al., "Specific RNA binding to ordered phospholipid bilayers" Nucleic Acids Research, 2006, vol. 34. No. 7, pp. 2128-2136.
Wong, B.C.K., et al., "Plasma RNA Integrity Analysis" Annals New York Academy of Sciences, p. 174-178, 2006.
Baj-Kryworzeka, M., et al., "Platelet-derived microparticles stimulate proliferation, survival, adhesion, and chemotaxis . . . " Experimental Hematology, 2002, vol. 30, pp. 450-459.
C:EPOPROGS\SEA\\ . . . XP-002456318, 2007.
Clotilde Thery et al. "Proteomic Analysis of Dendritic Cell-Derived . . . " The Journal of Immunology, p. 7309-7318, 2001.
Basyuk, E., et al., "Retroviral Genomic RNA's are Transported to . . . " Developmental Cell, Jul. 2003, vol. 5, pp. 161-174.
Gosert, R., et al., "RNA replication of mouse hepatitis virus takes place at . . . " Journal of Virology, Apr. 2002. pp. 3697-3708.
Bache, K.G., et al., "Hrs regulates multivesicular body formation via ESCRT . . . " The Journal of Cell Biology, Nov. 3, 2003, vol. 162, pp. 435-442.
Koga, K., et al., "Purification, characterization and biological significance of tumor-derived exosomes", Anticancer Research, Nov.-Dec. 2005, vol. 25, No. 6A, pp. 3703-3707.
Almstrup, K., et al., "Embryonic Stem Cell-Like Features of Testicular Carcinoma in Sity Revealed by Genome-Wide Gene Expression Profiling", Cancer Research, Jul. 15, 2004, vol. 64, pp. 4736-4743.
Chiou, S.H., et al., "Positive Correlations of Oct-4 and Nanog in Oral Cancer Stem-Like Cells and High Grade Oral Squamous Cell Carcinoma", Clinical Cancer Research, Jul. 1, 2008, vol. 14, pp. 4085-4095.

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(22)
<223> OTHER INFORMATION: Forward Primer for Her-2 (ERBB2)
```

```
<400> SEQUENCE: 1
atttctgccg gagagctttg at                                              22

<210> SEQ ID NO 2
<211> LENGTH: 22
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(22)
<223> OTHER INFORMATION: Reverse primer for Her-2 (ERBB2)

<400> SEQUENCE: 2
ccggccatgc tgagatgtat ag                                              22

<210> SEQ ID NO 3
<211> LENGTH: 22
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(22)
<223> OTHER INFORMATION: Forward primer for Her-2 (ERBB2)

<400> SEQUENCE: 3
gtgacagcag aggatggaac ac                                              22

<210> SEQ ID NO 4
<211> LENGTH: 19
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: Reverse primer for Her-2 (ERBB2)

<400> SEQUENCE: 4
cgccattgtg cagaattcg                                                  19
```

US 8,476,017 B2

MICROVESICLE-BASED COMPOSITIONS AND METHODS

This application is a continuation of U.S. patent application Ser. No. 12/488,110 filed Jun. 19, 2009 which is a continuation-in-part application of U.S. patent application Ser. No. 11/569,757 filed Nov. 29, 2006, which is a national phase application of our International Application No. PCT/US05/10674, filed Mar. 30, 2005, which claims priority to U.S. Provisional Application No. 60/576,395 filed Jun. 2, 2004. U.S. Patent Application No. 12/488,110 also claims priority to U.S. Provisional Application No. 61/074,218 filed Jun. 20, 2008. All priority documents are incorporated by reference herein.

FIELD OF THE INVENTION

The field of the invention is detection and/or analysis of RNA in microvesicles and their use in diagnosis, prognosis, and/or research of diseases and other conditions.

BACKGROUND OF THE INVENTION

Microvesicles were historically regarded as cellular debris with no apparent function. However, a growing body of experimental data has suggested that microvesicles have numerous biological activities. For example, platelet-derived microvesicles were shown to stimulate selected cells via surface proteins on the microvesicles (e.g., Thromb. Haemost. (1999), 82:794, or J. Biol. Chem. (1999), 274:7545). In other examples, specific effects of bioactive lipids in platelet microvesicles on certain target cells were reported (e.g., J. Biol. Chem. (2001), 276: 19672; or Cardiovasc. Res. (2001), 49(5):88). In still further examples, platelet microvesicles increased adhesion of mobilized CD34+ endothelial cells by transfer of certain microvesicle surface components to the mobilized cells (e.g., Blood (2001), 89:3143).

More recently, microvesicles have also been shown to comprise RNA that at least in part appeared to reflect the RNA content of the cell from which they originate. Microvesicles have also been shown to have significant biological effect on other cells, probably due to the RNA present in the microvesicles, and various examples and aspects for such microvesicles are described in our commonly owned International application (WO2005/121369), which expressly forms part of this application.

In further known reports, microvesicles were described as including non-coding miRNA (microRNA) that could potentially interfere or regulate gene expression in cells with which such microvesicles merge (PLoS November 2008, Vol. 3(11), e3694). Other reports discuss in vitro cell-to-cell signaling via exosomal RNA (Cell Adh Migr 1:3, 156-158; 2007; Cancer Immunol Immunother 2006 July; 55(7):808-18; Blood. 2007 Oct. 1; 110(7):2440-8.). It was also shown that while some exosomal RNA was functional and translatable in a recipient cell, many of the RNA molecules present in the exosomes were not present in the cytoplasm of cells from which the exosomes were though to have originated (Nat Cell Biol. 2007 June; 9(6):654-9). U.S. Pat. No. 6,916,634 teaches that while RNA is generally instable in serum and readily hydrolyzed by RNAses, other RNA is resistant to RNAse attack, presumably due to its varying association with circulating particles. Remarkably, the '634 patent elaborates on the chemically and structurally highly diverse nature of the RNA associated particles (presumably due to their diverse origin and manner of generation) and thus concludes that serum RNA is best isolated in an indiscriminate manner. Thus, even though membrane associated or vesiculated RNA has more recently been reported, there is a large body of contradictory data and hypotheses with respect to the nature, quality, availability, and origin/manner of generation of microvesicles.

Consequently, the enormous diagnostic potential of RNA-containing microvesicles has not been fully recognized in the art, and there is still a need for microvesicle-based diagnostic compositions and methods in which RNA from microvesicles is enriched and differentiated to so obtain a result that is indicative of the condition of tissue or organ from which the microvesicle originated.

SUMMARY OF THE INVENTION

According to the present inventive subject matter, microvesicles are employed in various diagnostic, prognostic, and/or analytic compositions and methods in which specific RNA content of microvesicles and optionally at least one more additional information bearing component of the microvesicle are used to obtain cell-, tissue-, organ-, and/or disease-specific information.

In one especially preferred aspect of the inventive subject matter, method of analyzing a biological sample (e.g., plasma or serum) of a mammal in which microvesicles are obtained from a living donor mammal (preferably human) that include a plurality of distinct RNA molecules. The microvesicles are then enriched and differentiated to produce a primary result based on one or more distinct RNA molecules, a secondary result based on at least two distinct RNA molecules, and/or a ternary result based on sub-segregated proxysomes and one or more distinct RNA molecules. Of course, it should be appreciated that the RNA analysis in the differentiation may include analysis of a single RNA, of at least two distinct RNAs, and in some aspects even an entire RNA profile (typically obtained by analysis of an array of multiple distinct DNA or RNA). The so obtained results are then correlated with a diagnosis (e.g., cancer or a clinical stage of a cancer, including pre-cancerous stages) or prognosis/diagnosis of a condition of the mammal.

Most typically, the distinct RNA molecule(s) in the primary result is/are RNA that is overexpressed, underexpressed, and/or mutated, wherein the change in expression and/or the mutation is characteristic for the condition. Similarly, one of the two distinct RNA molecules in the secondary result is an RNA that are overexpressed, underexpressed, and/or mutated, wherein the change in expression and/or the mutation is characteristic for the condition, while the other of the distinct RNA molecules in the secondary result is an RNA that is uniquely expressed in a specific tissue or organ of the mammal. The sub-segregated proxysome population is preferably obtained by isolating the proxysome population based on a surface molecule specific for origin of the proxysome population, and the distinct RNA molecule in the ternary result is RNA that is overexpressed, underexpressed, and/or mutated, wherein the change in expression and/or the mutation is characteristic for the condition.

With respect to the RNA that is overexpressed, underexpressed, and/or mutated, it is typically preferred that the RNA encodes MMP11, BCAR1, ERBB2, MKI67, PLAU, and/or TP53 where the condition is breast cancer; or encodes FGFR1, KRAS2, TGFBR2, MAP2K4, and/or CDKN2A where the condition is pancreatic cancer; or encodes KLK3, ERBB2, FGF8, PSCA, and/or CAV1 where the condition is prostate cancer; or encodes BAX, SLC2A1, PTGS2, MUC1, and/or RUNX3 where the condition is gastric cancer; or encodes BCL10, PAP, SPARC, CD44, and/or TP53 where the condition is liver cancer; or encodes a stem cell marker, and especially an adult stem cell marker (e.g., CD33, CD44, CXCR4, CXCR4+, lin−, CD45−, Oct-4, Nanog, SCA1, 7-AAD), where the condition is a cancer.

With respect to the RNA that is uniquely expressed in the specific tissue or organ it is preferred that the RNA encodes DCD, SCGB2A2, and/or ANKRD30A where the specific tissue or organ is breast tissue; or encodes UCN3, IPF1, and/or REG1B where the specific tissue or organ is a pancreas; or encodes UPK3A, SEMG1, and/or PRAC where the specific tissue or organ is prostate tissue; or encodes GAST, GKN1, and/or TFF2 where the specific tissue or organ is gastric tissue; or encodes GYS2, F9, and/or HRG where the specific tissue or organ is a liver.

It is further generally preferred that the microvesicles are enriched via aggregation by interlinking the microvesicles with an interlinking composition (e.g., annexin V, fibrin, or an antibody or antibody fragment against a tetraspanin, ICAM-11, or CD86). Consequently, microvesicles especially contemplated herein have a membrane composition such that phosphatidylserine is on the outside of the membrane. It is further generally preferred that the primary or secondary result are obtained using a quantitative rtPCR for the distinct RNA molecule or via microarray technology.

Thus, viewed from a different perspective, a method of staging a mammalian neoplasm (which also includes staging of precancerous lesions or growth) will include a step of obtaining a whole blood fraction (e.g., serum or plasma) that includes a plurality of microvesicles comprising a plurality of distinct RNA molecules. In another step, the microvesicles are enriched (e.g., via centrifugation and/or aggregation) and differentiated (e.g., using quantitative rtPCR) to produce a primary result based on at least one distinct RNA molecule, a secondary result based on at least two distinct RNA molecules, and/or a ternary result based on a sub-segregated proxysome population and at least one distinct RNA molecule. The results are then correlated with a stage of the neoplasm in the mammal, typically via comparison with a reference result.

Among other neoplasms, especially contemplated neoplasms include acute lymphoblastic leukemia, bladder cancer, breast carcinoma, cervical cancer, colorectal cancer, lung cancer, ovarian cancer, and pancreatic adenocarcinoma. Therefore, one of the at least two distinct RNA molecules in the secondary result or one of the distinct RNA molecules in the primary or ternary result will be an RNA that encodes ERBB2.

Various objects, features, aspects and advantages of the present invention will become more apparent from the following detailed description of preferred embodiments of the invention.

DETAILED DESCRIPTION

Figure 1:
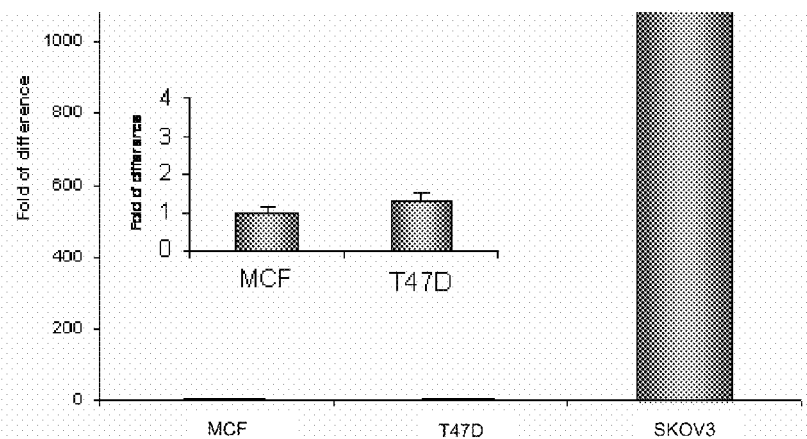
FIG. 1 is a graph depicting the results for in vitro expression of Her2-RNA in selected cell lines.

The inventor has discovered that mammalian, and especially human microvesicles can be employed as a proxy diagnostic tool in the analysis and/or diagnosis of a cell, tissue, organ, or even multi-organ system where RNA and/or multiple non-RNA components (e.g., soluble and/or membrane proteins, lipids, etc.) from the microvesicles are correlated with status and/or health of the cell, tissue, organ, or even multi-organ system from which the microvesicle originated. Based on the inventor's findings that the RNA content of the microvesicles is entirely or almost entirely representative of the cellular RNA of the cell from which the microvesicle originated, numerous uses are now envisioned. As microvesicles are shed by all cells in relatively high numbers, and as microvesicles are also present in equally high number in blood, the inventor concluded that, inter alia, gene expression, soluble/membrane proteins, and membrane composition of various cells, tissues, and organs can be easily determined by analyzing the corresponding microvesicles, where those microvesicles are obtained from a biological fluid, and especially blood.

The term "microvesicle" as used herein refers to a membranaceus particle having a diameter (or largest dimension where the particle is not spheroid) of between about 10 nm to about 5000 nm, more typically between 30 nm and 1000 nm, and most typically between about 50 nm and 750 nm, wherein at least part of the membrane of the microvesicle is directly obtained from a cell. Therefore, especially contemplated microvesicles include those that are shed from a donor cell, and will typically also include exosomes. Therefore, and depending on the manner of generation (e.g., membrane inversion, exocytosis, shedding, or budding), the microvesicles contemplated herein may exhibit different surface/lipid characteristics. Viewed from a different perspective, the microvesicles suitable for use in the present inventive subject matter may originate from cells membrane inversion, exocytosis, shedding, blebbing, or budding. Most typically, microvesicles suitable for use herein will be identifiable by having phosphatidylserine, a tetraspanin, ICAM-1, and/or CD86 on the outer surface. In contrast, a liposome made from isolated lipids will not include lipids or other components obtained from a cell-membrane, and is not considered a microvesicle under the definition used herein. Therefore, most typically, contemplated microvesicles will have a lipid bilayer structure and are not multi-lamellar.

Moreover, it is preferred that the microvesicles are generated from a differentiated cell, and most preferably from a terminally differentiated cell (i.e., a cell that has reached the end of its differentiation pathway). Therefore, microvesicles generated by blast cells, progenitor cells, and stem cells are excluded in at least some of the embodiments herein. However, and especially where the microvesicles are generated from a cancer cell, and where that cancer cell is derived from an adult stem cell (as opposed to an embryonic stem cell) less differentiated cells are also deemed suitable sources for the microvesicles. It is especially preferred that the microvesicles are derived from cells that are diseased (e.g., neoplastic cell, infected cell, cell in an infected organ) or subject to an abnormal condition (e.g., metabolic abnormality, cell exposed to a drug, and more typically a drug that preferentially affects the cell relative to other cells, or dietary toxin, or damaged by free radicals). In still further contemplated aspects, the microvesicles are generated from a healthy, but ageing cell, i.e., a cell that has reached at least 50%, and more typically at least 70% of its ordinary number of cell divisions (Hayflick limit). It should be noted that synaptosomes (vesicular entities in the synaptic gap, but not present in the general circulation) and microvesicles that are formed from platelets are expressly excluded.

Thus, the RNA content of the microvesicles is thought to be characteristic of a particular condition (e.g., disease, age, stress, response to a chemical compound, senescence, inflammation, infection [e.g., viral, microbial, parasitic], immune status, regeneration, rejection, etc.). Non-RNA information bearing components in microvesicles contemplated herein include various proteins (e.g., receptor, ligand, glycoprotein, etc.) that are associated with the microvesicle, which may be at least partially embedded in the membrane (or even be entirely enclosed), specific lipids or glycolipids that are associated with the microvesicle, and/or a further nucleic acid (DNA and/or RNA) associated with the microvesicle. Thus, and especially where the non-RNA information bearing component is specific to a particular organ, tissue, and/or cell, analysis of the condition of the particular organ, tissue, and/or cell can be obtained in a highly simplified and even multiplexed manner. Consequently, and among other advantages, it should be especially appreciated that a serum or blood based test can be performed that provides (even multiple) organ specific results without the need for an otherwise required organ-specific biopsy. Still further, it should be noted that the methods contemplated herein will allow virtually unlimited and repeated real time access to an expression profile of the same tissue or organ.

Consequently, methods according to the inventive subject mater will typically include the following sequence (in which one or more steps may be combined):

Isolation→Differentiation→Analysis.

More specifically, and in one particularly preferred example, the inventor contemplates a method of analyzing a biological sample of a mammal in which a plurality of microvesicles that include distinct RNA molecules is first obtained from a living donor mammal. The microvesicles are then enriched and differentiated to produce a primary result based on one or more distinct RNA molecules (which are most typically a RNA that are uniquely expressed and/or mutated as a function of the condition of the cell from which it derived), a secondary result based on at least two distinct RNA molecules (with one of the molecules being RNA that is uniquely expressed in a specific tissue or organ, and with the other molecule being RNA that is uniquely expressed and/or mutated as a function of the condition of the cell from which it derived) and/or a ternary result based on a sub-segregated proxysome population (e.g., based on a specific surface marker of the cell from which the microvesicle was derived) and one or more distinct RNA molecules (most typically a RNA that is uniquely expressed and/or mutated as a function of the condition of the cell from which it derived). The primary, secondary, and/or ternary results are then correlated with a diagnosis or prognosis of a condition of the mammal.

Most typically, the microvesicles are obtained from whole blood, serum, plasma, or any other biological fluid, including urine, milk, tears, spinal fluid, amniotic fluid, etc., which are preferably obtained from a living mammal, and most preferably within the time limit acceptable for processing biological fluids for later clinical analysis. Alternatively, in less preferred aspects, microvesicles may also be obtained from stored materials (e.g., biological fluids, tissues, organs, etc.), wherein the time between obtaining the biological fluid, tissue, or organ, and enrichment of the microvesicles from the sample may be at least 12 hours, at least 24 hours, at least 2-5 days, or even at least one or more weeks. Such storage may even include storage at reduced temperature (e.g., 4° C.) or even storage in frozen form. Similarly, microvesicles may also be obtained from an in vitro source, and most typically from cell or tissue culture, or even organ culture. In yet further contemplated aspects, it should be noted that deceased donors are also deemed suitable as a source for the microvesicles. Most commonly, however, microvesicles will be obtained from blood, which may be immediately or within a few hours (less than 12 hours) processed to form serum or plasma, which is then either stored, shipped, and/or further processed o enrich the microvesicles.

With respect to isolation or enrichment of microvesicles it is contemplated that all known manners of isolation of microvesicles are deemed suitable for use herein. As used herein, the terms "isolation" or "isolating" in conjunction with microvesicles are interchangeably used with the terms "enrichment" or "enriching", and refer to one or more process steps that result in an increase of the fraction of microvesicles in a sample as compared to the fraction of microvesicles in the obtained biological sample. Thus, microvesicles may be purified to homogeneity, purified to at least 90% (with respect to non-microvesicle particulate matter), less preferably at least 80%, even less preferably at least 50%, and least preferably at least 20% (or even less). For example, physical properties of microvesicles/proxysomes may be employed to separate them from a medium or other source material, and especially preferred physical methods include separation on the basis of electrical charge (e.g., electrophoretic separation), size (e.g., filtration, molecular sieving, etc), density (e.g., regular or gradient centrifugation), Svedberg constant (e.g., sedimentation with or without external force, etc). Alternatively, or additionally, isolation may be based on one or more biological properties, and especially suitable isolation methods may employ surface markers (e.g., for precipitation, reversible binding to solid phase, FACS separation, specific ligand binding, non-specific ligand binding such as annexin V, etc.). In yet further contemplated methods, the microvesicles may also be fused using chemical and/or physical methods, including PEG-induced fusion and/or ultrasonic fusion.

Viewed from a different perspective, enriching can be done in a general and non-selective manner (typically including serial centrifugation), and may be performed by aggregation where the microvesicles are interlinked with an interlinking composition (e.g., annexin V, fibrin, or an antibody or fragment thereof against at least one of a tetraspanin, ICAM-1, and CD86). Alternatively, enriching can be done in a more specific and selective manner (e.g., using tissue or cell specific surface markers). For example, specific surface markers may be used in immunoprecipitation, FACS sorting, bead-bound ligands for magnetic separation etc. Such isolation or enrichment will advantageously allow obtaining cell-, tissue-, organ-, and/or disease specific information without the need for direct access to the cell, tissue, or organ under investigation. The specific RNA that is enclosed in a general population of microvesicles is therefore generally termed "vesiculated RNA", while RNA of a specific type of microvesicle (e.g., microvesicle generated by hepatocyte) is termed "proxy RNA", and microvesicles that are specific to a single type of origin are referred to as "proxysomes". Such proxysomes will consequently have an RNA content and membrane composition (especially in terms of surface markers, but also to at least some degree in terms of lipid composition) that is consistent with the RNA content of a cell from which the proxysome is produced.

Therefore, and especially where the microvesicles/proxysomes are isolated from a biological source (e.g., whole blood or serum) or mixed cell or tissue culture, it should be noted that the isolation may produce a heterogeneous population of microvesicles/proxysomes with respect to the cell-/tissue-, and/or organ-type from which the microvesicles/proxysomes were produced. On the other hand, and especially where a specific surface marker was used in the isolation of the microvesicles/proxysomes, the isolated population may already be homogenous with respect to the cell-/tissue-, and/or organ-type from which the microvesicles/proxysomes were produced. In still further contemplated aspects, the mechanism of release of the vesicles from the cell may be used to further differentiate, even among proxysomes. However, it should be noted that all vesicular architectures (e.g., inside-out, etc.) are deemed suitable for use herein.

As a population of microvesicles obtained from a biological fluid will typically represent a plurality of cells, tissues, and organs, differentiation of the heterogeneous population is often desirable to obtain a cell, tissue, or organ specific result. Differentiation of the microvesicles is typically dependent on the type of cell, tissue, or organ under investigation, and conceptually at least three distinct approaches can be taken.

First, where a condition (e.g., cancer, infection, senescence, inflammation, etc.) of a cell, tissue, or organ is associated with a unique and distinguishable expression profile (e.g., over- or underexpression) of a gene and/or with a specific mutation, a meaningful result may be based on the expression profile and/or specific sequence of one or more distinct RNA molecules without further normalization of the signal. For example, where the condition is breast cancer, several genes are often misregulated, and presence of high quantities of ERBB2 will be indicative of breast cancer. Similarly, certain types of leukemia (CML) are associated with a specific fusion mutant (Bcr/Abl) that is specifically associated with the leukemia. Thus, a primary result can be obtained based on the expression profile and/or specific sequence of one or more distinct RNA molecules without physical sub-segregation of the microvesicles.

Second, a condition (e.g., cancer, infection, senescence, inflammation, etc.) of a cell, tissue, or organ may be associated with a unique and distinguishable cell, tissue, or organ type and may therefore be specifically characterized by normalizing an expression profile and/or specific sequence of one or more distinct RNA molecules against the expression profile and/or specific sequence of one or more further distinct RNA molecules that are uniquely present or expressed in the specific cell, tissue, or organ. Thus, a secondary result can be obtained based on the expression profile and/or specific sequence of at least two distinct RNA molecules without physical sub-segregation of the microvesicles.

Third, a condition (e.g., cancer, infection, senescence, inflammation, etc.) of a cell, tissue, or organ may be associated with a unique and distinguishable cell, tissue, or organ type and may therefore be specifically characterized by physical sub-segregation (infra) of the microvesicles prior to analysis of the expression profile and/or specific sequence of one or more distinct RNA molecules in the sub-segregated microvesicles.

Therefore, in some aspects of the inventive subject matter, differentiation is preferably done using one or more additional information bearing components in and/or on the microvesicle to correlate the result with the additional information to so obtain normalized cell-, tissue-, organ-, and/or disease-specific information. Viewed from a different perspective, differentiation may therefore include a sub-segregation of a subset of proxysomes from the microvesicles, and/or a determination of a reference marker that is specific to a subset of proxysomes of the isolated population. It should be especially appreciated that the differentiation may also include detection or use of a component (or portion thereof) on a microvesicle or proxysome that is otherwise not accessible on the cell. Such is especially true where the microvesicle or proxysome has an inside-out architecture that exposes on the outside of the microvesicle or proxysome the component that has an orientation normally oriented towards the interior of the cell from which the vesicle is produced.

For example, where differentiation is based on molecular analysis of gene expression of a gene that is significantly associated with a particular disease, differentiation may be based on the unique sequence, expression profile, mutation, or other character of a particular RNA and thus will typically not require physical subsegregation and/or normalization against other RNA and/or protein markers. Thus, in at least some instances, presence, abundance, and/or sequence of one or more RNA molecules in the microvesicle population can be directly attributed to a specific disease or condition of a cell, tissue, or organ. For example, where a patient is suspected of breast cancer the presence, specific sequence, and/or expression rate of a relevant oncogene (e.g., BRCA, Her2/neu, etc.) in a microvesicle will be useful as a proxy marker for the cancer as such particular RNA is normally not present in measurable quantities in microvesicles.

Alternatively, and especially where an RNA under investigation is present in diseased (or otherwise compromised) as well as healthy cells, tissues, or organ, differentiation may be based on normalization of the RNA under investigation against one or more other constituent parts of the microvesicles/proxysomes. Therefore, it should be appreciated that differentiation can be performed on a non-segregated pool of microvesicles, and even on the source material where the microvesicles are present. In such case, it is generally preferred that the additional information bearing component is specific to a particular subset of proxysomes. For example, it is of interest to analyze microvesicles from mammary gland tissue, a gene may be identified that is uniquely (greater or equal 90%) or predominantly (greater or equal 75%) expressed in the mammary gland tissue. As the proxysome RNA content is an at least partial, and in many cases a complete representation of the RNA content of the mammary gland cell from which the proxysome is derived, the mammary gland proxysome is expected also to comprise the uniquely or predominantly expressed gene. For example, it is known that dermcidin is >95% selectively expressed in mammary gland tissue and therefore also expected to be uniquely present in mammary gland proxysomes. There are numerous genes known in the art that are uniquely or predominantly expressed in specific cells and organs, and suitable genes with such expression can be found, inter alia, at the TIGER database (http://bioinfo.wilmer.jhu.edu/tiger/; incorporated by reference herein).

Alternatively, or additionally, numerous known non-nucleic acid components can be used to differentiate and may include disease specific markers (e.g., tumor specific markers such as CEA), organ specific markers (e.g., PSA), and/or cell-specific markers (e.g., CD4 for T-helper cells), etc. These additional information bearing components may then be used for physical subsegregation in a manner as described above. However, it is also noted that so long as these additional information bearing components are specific to the desired subpopulation of proxysomes, no physical subsegregation may be required, and the RNA information (infra) may be normalized or otherwise parameterized using the additional information bearing component. Thus, it should be recognized that molecular analysis for differentiation can be done with high specificity to a particular cell type, tissue type, and/or organ type.

Physical subsegregation of a subset of proxysomes may be performed using antibodies or other binding agents that binds selectively to a component that is specific to particular cell, tissue, or organ. Such components are typically cell-, tissue-, or organ-specific marker, receptors, structural components, glycoproteins, CDs, etc., all of which may be further derivatized. Suitable organ, tissue, and cell specific surface markers are well known in the art and can be found in numerous publications (e.g., for natural receptors see e.g., Cell Surface Receptors: A Short Course on Theory and Methods by Lee E. Limbird Springer; 2nd ed. edition (Dec. 31, 1995), ISBN-10: 0792338391; for synthetic peptides to selected cells, see e.g., Curr Opin Chem Biol. 2000 February; 4(1):16-21). Thus, it should be appreciated that subsegregation can be performed specific to a cell type, tissue type, and/or organ type.

Most typically, physical subsegregation will involve use of a solid phase to which a compound is bound that (preferably releasably) binds to one or more of the component that is specific to particular cell, tissue, or organ. For example, where the solid phase is a multi-well plate, proxysomes may be separated into separate wells. Where the solid phase is a magnetic or color coded bead, the proxysomes may be isolated using a magnet or light activated sorter. Similarly, the solid phase may be a dipstick or membrane and separation will (preferably releasably) bind the proxysomes on the solid phase. In still further contemplated aspects, subsegregation may also be performed on an array in which antibodies are coupled to the surface of the array in predetermined positions to so specifically bind distinct proxysomes in distinct and predetermined positions on the array. Detection of the bound proxysomes may then be performed in a non-specific manner (e.g., using a labeled form of annexin V) or a specific manner (e.g., using a labeled antibody against another surface marker of the proxysome).

Of course, it should be recognized that subsegregation may be done after isolation of a population of microvesicles, but may also be directly performed on the source material of the microvesicles/proxysomes. In such case, the steps of isolation and subsegregation are combined. Most typically, and depending on the surface marker used, the subsegregation will produce a subpopulation of proxysomes that is substantially homogeneous (i.e., at least 70%, more typically at least 80%, most typically at least 90%) with respect to the tissue from which they originate (e.g., microvesicle from liver, prostate, mammary gland, etc.). It should further be especially appreciated that the subsegregation may also be performed (e.g., without RNA analysis) to determine numerical ratios and/or absolute numbers of microvesicles/proxysomes.

The specific RNA of the proxysome of interest can most typically be analyzed using all known manners of RNA analysis, and particularly preferred manners include rtPCR, quantitative PCR (rt or otherwise), primer extension analysis (with or without prior amplification), and all solid-phase based methods (e.g., using arrays, magnetic or color coded beads, etc.). While not limiting to the inventive subject matter, it is generally preferred that the specific RNA is (1) native to the cell, tissue or organ, i.e., not introduced (directly or indirectly) by a pathogen, and/or (2) specific or indicative to a predisposition, condition, disease, response to a stimulus, and/or pathogen. For example, suitable specific RNAs include genes that are specifically and exclusively expressed or overexpressed in cells, tissues, or organs affected with a neoplastic disease, a metabolic disease, inflammation, senescence, hypoxia, an infection, and/or inheritable disease.

For example, especially suitable specific RNAs are those known to have an association with a particular disease and especially with cancer. There are numerous such RNAs and genes known in the art, and all of those are deemed suitable for use herein. Among other sequences, RNA specific for breast cancer includes RNA that encodes MMP11, BCAR1, ERBB2, MKI67, PLAU, and/or TP53, RNA specific for pancreatic cancer includes RNA that encodes FGFR1, KRAS2, TGFBR2, MAP2K4, and/or CDKN2A, RNA specific for prostate cancer includes RNA that encodes KLK3, ERBB2, FGF8, PSCA, and/or CAVI, or RNA specific for gastric cancer includes RNA that encodes BAX, SLC2A1, PTGS2, MUC1, and/or RUNX3, RNA specific for liver cancer includes RNA that encodes BCL10, PAP, SPARC, CD44, and/or TP53, and RNA found for various cancers includes RNA that encodes adult stem cell markers (e.g., CD33, CD44, CXCR4, CXCR4+, lin−, CD45−, Oct-4, Nanog, SCA1, and/or 7-AAD. Further numerous cancer related genes/RNA can be found in various publicly or commercially available database (e.g., http://www.cancerindex.org/geneweb/clink30.htm, incorporated by reference herein). In still further especially preferred aspects, it is contemplated that more than one specific RNA is measured to so improve a diagnostic finding. For example, where paired or grouped markers are analyzed, ERBB2 and VEGFR may be measured in a population of proxysomes from mammary gland tissue.

Of course, it should be noted that the RNA of interest need not be limited to an RNA that is associated with a particular disease, but that suitable information may be generated from analysis of the expression pattern on of or more distinct RNAs. For example, it is contemplated that total RNA from a non-segregated microvesicle population is analyzed on a chip of other multiplexed platform to so arrive at a genome wide expression profile. Such expression profile may then be used as a basis for diagnosis of a condition or disease where an expression profile of a healthy individual is known. Consequently, it should be appreciated that for the first time, one or more systemic expression profiles may be obtained from the same individual (or group of individuals) in a manner that does not require multiple biopsies. Similarly, and especially where the RNA analysis is normalized against a specific tissue or performed on a sub-segregated population of microvesicles, tissue specific expression profiles may be obtained from the same individual (or group of individuals) in a manner that does not require biopsies.

While not expressly excluded, it is generally preferred that the RNA is an RNA that is coding and can give rise to a protein via ribosomal translation. Therefore, most typically RNA will include a 3'-polyA tail and may further include a 5'-cap structure (typically 7-methylated guanine nucleotide bound to mRNA via 5'-5' triphosphate group, but less common structures also deemed suitable and include methylation of the 2' hydroxy-groups of the first 3 ribose sugars of the 5' end of the mRNA). Furthermore, it should also be noted that while mRNA is deemed especially useful in conjunction with the teachings presented herein, other forms of RNA are also expressly contemplated herein. For example, suitable RNA for analysis include single stranded and double stranded RNA, heterogenous RNA (hnRNA), small interfering RNA (siRNA), transfer RNA (tRNA), ribosomal RNA (rRNA), mitochondrial RNA (mtRNA), capped RNA and uncapped RNA, polyadenylated and non-polyadenylated RNA, etc.

Analysis of the specific RNA and the additional information bearing component is based on the premise that each proxysome will have at least one RNA specific for a disease/ condition and at least one additional representative component of the cell from which that proxysome was produced (e.g., RNA of a tissue-specific expressed gene, a cytoplasmic component, a membrane composition, membrane associated component (typically comprising a protein). Together, the specific RNA and the additional component (which may be another RNA that is cell- or tissue specific, a protein, a lipid, or any combination thereof) are then employed to analyze a condition (e.g., disease or predisposition, age, reaction to physical or chemical stimulus [e.g., drug, food, radiation, etc.]) in a highly cell-, tissue-, and/or organ-specific manner without the need to directly sample the cell-, tissue-, and/or organ. Analysis may be typically be specific with respect to a set of markers. However, analysis may also be analyzed as a function of time to see fluctuations in total microvesicles and/or proxysomes or proxysome populations. Analysis may be focused on time course, quantity, and/or association with further markers. Thus, analytic results will typically include variants, quantities, and/or or time course expression of the specific RNA, which will most typically be correlated with one or more results obtained from the differentiation (which may be a quantitative measure of mRNA, a peptide, a membrane component, etc.).

With respect to analysis of the additional information bearing component it should be appreciated that those components can be analyzed (or used) in all known manners. For example, where the additional information bearing component comprises a peptide, especially preferred manners include use of antibodies (or fragments thereof), ligands (synthetic or natural), etc., all of which may be labeled or otherwise modified for qualitative or quantitative analysis. Where the additional information bearing component is a polysaccharide, lectins may be used, and where the additional information bearing component is a lipid, specific ligands (e.g., annexin V) may be used for quantification. Moreover, and especially where the additional information bearing component is a compound other than a nucleic acid, it is contemplated that the additional information bearing component may be used to sub-segregate a population of microvesicle into a population that is enriched in one specific type of microvesicle (enrichment preferably >80%).

Depending on the particular RNA and manner of differentiation, it should be appreciated that the manner of correlation of the results to a specific diagnosis or condition may vary to at least some degree. For example, where the analysis of RNA relies on quantification and/or sequence of a disease-specific gene, correlation may advantageously be done by comparison of the result(s) with result(s) obtained from a microvesicle population obtained from a reference patient (which may be healthy, or representative to a specific disease stage or state). Similar correlation can be performed for tests in which the RNA is normalized against another RNA or non-RNA compound from a microvesicle, or is normalized mcg of total RNA/mL of serum, total RNA per mg of MVs proteins isolated from 1 mL of serum, or other preferably fixed parameter. In like manner, where the RNA is obtained from a population of proxysomes, correlation is typically performed against a known standard that is indicative for a particular disease or condition. Of course, it should be appreciated that the comparison of the results may be performed one a single RNA basis, on the basis of two or more RNA results, or in at least some cases, on a genome or organ-specific basis. In such case, the correlation will include comparison of multiple RNA-specific results with multiple reference results, and all possible cross-relations thereof Thus, it should be appreciated that the inventor especially contemplates a method of confirming and/or staging a mammalian neoplasm in which in one step a whole blood fraction is obtained that includes a plurality of microvesicles comprising a plurality of distinct RNA molecules. In another step the microvesicles are enriched and differentiated to so produce a primary result based on one or more distinct RNA molecules, a secondary result based on at least two distinct RNA molecules, and/or a ternary result based on a sub-segregated proxysome population and at least one of the plurality of distinct RNA molecules. In yet another step, the primary, secondary, and/or ternary results are correlated with a stage of the neoplasm in the mammal.

Generally all neoplasms are deemed suitable for use herein (supra), however, it is particularly preferred that the neoplasm is characterized by overexpression (relative to healthy cell) of ERRB2. Consequently, suitable neoplasms include acute lymphoblastic leukemia, bladder cancer, brain cancer, breast carcinoma, cervical cancer, colorectal cancer, lung cancer, ovarian cancer, and pancreatic adenocarcinoma. RNA coding for ERRB2 overexpression can be quantified in numerous manners, however, it is generally preferred that the step of differentiating comprises quantitative rtPCR and/or reverse transcription and solid phase (e.g., microarray) hybridization. As already noted above, it is generally preferred that the step of correlating comprises comparison of the primary, secondary, and/or ternary results with one or more reference results that are characteristic of a healthy cell and/or a diseased cell, tissue or organ in a specific diseased, compromised, or aged state.

Viewed from a different perspective, contemplated uses of diagnostic tests and compositions include diagnosis, predisposition, and prognosis of the metabolic state of a cell, tissue, and/or organ, analysis of the response of a cell, tissue, and/or organ to a physical and more typically chemical stimulus, and/or diagnosis or determination of predisposition for a disease or disorder in patient harboring a cell, tissue, and/or organ from which the proxysomes were analyzed. In especially preferred uses, the methods according to the inventive subject matter are employed in the diagnosis of cancer, a pre-cancerous condition or predisposition, and/or a clinical stage of a cancer. Additionally, it should be noted that contemplated methods are also deemed suitable for prenatal diagnosis as fetal microvesicles have been identified in (Kidney International, 2007; 72(9):1095-102) amniotic fluid, placenta, and possibly also blood of the pregnant mother.

In still further contemplated uses, it should be appreciated that microvesicle/proxysome compositions and methods according to the inventive subject matter can be used in bioinformatic analysis in which 'normal' proxysome quantity and composition is acquired and then compared to proxysome quantity and composition from cells treated with one or more agents or conditions. Wile contemplated compositions and methods typically reply on already known specific RNAs and additional markers and information bearing components, it should be appreciated that new specific RNAs and new information bearing component can be relatively easy obtained. For example, a cell culture of diseased cells or cells from a disease model can be propagated in vitro. The supernatant is then collected and microvesicles are isolated from the supernatant. In an optional step, protein is extracted from the microvesicles and antibodies generated. The antibody collection is then subtracted against normal tissue to obtain disease specific antibodies. Alternatively corresponding experiments can be performed in silico based on expression profiling, or subtractive nucleic acid libraries of diseased and corresponding healthy cells can be generated.

In still further contemplated aspects, the microvesicle diagnostic methods presented herein can be advantageously employed in drug discovery where multiple cell cultures are separately exposed to multiple drugs. Genomics and proteomics analyses can be performed as known in the art. However, in preferred aspects, proxysomes can be collected from the individual cultures and analyzed as described above. The so obtained results can then be followed in vivo to ascertain that in vitro findings correlate with prior in vitro results. Moreover, as the microvesicles can be collected multiple times from a single animal and as a single collection is sufficient to analyze distinct reactions in multiple organs without sacrificing speed or accuracy (or the animal), drug discovery using proxysomes dramatically increases throughput in drug discovery. While it is generally preferred that analysis is performed using specific RNA(a) and additional information bearing components, it is also contemplated that the microvesicle/proxysome components can be analyzed in relative and absolute proportions to obtain a measure for a particular clinical parameter. It should still further be noted that while contemplated methods and compositions are particularly useful for clinical diagnostic purposes and R&D, the methods and compositions according to the inventive subject matter will may also be advantageously employed in personalized medicine and personalized nutrition in which the effect of administration of nutraceuticals (and medications) on microvesicles and proxysomes can be monitored in a highly simplified manner.

It should be appreciated that contemplated tests allow for standardization, which is one of the more significant hurdles in clinical diagnosis. In one aspect of the inventive subject matter, the RNA signal is normalized against a second signal, typically derived from the additional information bearing components (e.g., total signal from proxysome membrane [e.g., via labeled annexin V]). Alternatively, a range of normal can be established from a clinically healthy population, again using a signal from an additional information bearing component. For example, one could employ a known microvesicle ELISA (which measures amount of PS, phosphatidylserine), which is highly correlated with microvesicles. There is already normal range established in healthy individuals (about 10 Nm/ml), which may serve as a normalization signal. In such assay, RNA Her2 could be calculated per total microvesicles, measured PS, or HER2 RNA signal per (phosphatidylserine—Platelet microvesicles phosphatidylserine). If using realtime PCR, one would compare the number of cycles per phosphatidylserine. In case off an arras, the array signal is correlated to per phosphatidylserine.

EXAMPLES

The following is provided to illustrate exemplary methods, conditions, and embodiments in connection with contemplated methods and compositions, but should not be deemed limiting the inventive subject matter.

Detection of Her-2 Expression in Breast Cancer Cell Lines

Real time PCR: Three cancer cell lines were cultured in normal cell culture conditions (37° C., 5% CO2) according to respective ASTM standard protocols. Total RNA was isolated from the cells using the commercially available RNeasy isolation kit (QUIAGEN) according to manufacturer's protocol. After isolation, the concentration of total RNA was determined by UV spectroscopy using well established methods. The concentration of RNA was adjusted for all groups to 50 ng/mcl. So prepared RNA was reverse transcribed to cDNA using a commercially available reverse transcription kit (Applied Biosystems) following the manufacturer's protocol. This cDNA was then used for real time PCR studies. The real time PCR reaction contained Sybr green master mix, forward primer, reverse primer, water, and respective cDNA samples, and the following HER-2 primers were used (5'- to 3'-end):

Forward: ATTTCTGCCGGAGAGCTTTGAT    (SEQ ID NO: 1)
Reverse: CCGGCCATGCTGAGATGTATAG    (SEQ ID NO: 2)

Real time PCR reaction was performed with using Real Time PCR System ABI 7500 (Applied Biosystems), using following settings: 50° C. 2 min, 95° C. 5 min, 95° C. 15 sec, 60° C. 60 sec; Last two cycles were repeated 40 times. Relative quantitation of Her-2 mRNA expression was calculated with the comparative Ct method. The relative quantitation value of target, normalized to an endogenous control B2MG gene and relative to a calibrator, is expressed as $2^{-\Delta\Delta Ct}$ (fold difference), where $\Delta Ct = Ct$ of target gene, $-Ct$ of endogenous control gene (B2MG), and $\Delta\Delta Ct = \Delta Ct$ of samples for target gene $-\Delta Ct$ of calibrator for the target gene.

To avoid the possibility of amplifying contaminating DNA (i) all the primers for real time PCR were designed with an intron sequence inside cDNA to be amplified, (ii) all reactions were performed with appropriate negative controls (template-free controls), (iii) a uniform amplification of the products was rechecked by analyzing the melting curves of the amplified products (dissociation graphs), and (iv) gel electrophoresis was performed to confirm the correct size of the amplification and the absence of unspecific bands. The results for this experiment are shown in FIG. 1. As can be readily taken from the Figure, and as assessed via rtPCR, SKOV3 exhibited significant expression of Her-2 whereas Her-2 expression in T47D cells was moderate and nearly undetectable in MCF cells. This finding correlates well with published literature data on Her-2 expression in these cell lines.

Regular PCR: Using RNA isolated as described above, a regular PCR was performed. Briefly, RNA was reverse transcribed to cDNA with using Applied Biosystem reverse transcription kit following the manufacturer's protocol, and the so prepared cDNA was used for PCR studies. Regular PCR reaction used the following Her-2 primers (5'- to 3'-end):

Forward: GTGACAGCAGAGGATGGAACAC    (SEQ ID NO: 3)
Reverse: CGCCATTGTGCAGAATTCG       (SEQ ID NO: 4)

To avoid the possibility of amplifying contaminating DNA (i) all the primers for PCR were designed with an intron sequence inside cDNA to be amplified, and the (ii) reactions were performed with appropriate negative controls (template-free controls). The PCR products were visualized using a 1.5% agarose gel. Once more, Her-2 was detectable in the mRNA level in all three cell lines, but SKOV3 cell lines showed highest expression, and T47D cells and MCF cells showed expression on very low level. Negative controls were performed using RNA without reverse transcription, and PCR products were not detected.

Detection of Her-2 in Microvesicles from Supernatants of the Cell Lines

Isolation of Microvesicles: The tumor derived microvesicles were isolated from culture conditioned media. Briefly, the supernatant was spun at about 850 g for 10 minutes at 4° C. The supernatant was collected and the pellets were discarded. The supernatants were again spun at 24,000 g for 2 hr at 4° C. and the supernatant was discarded. PBS supplemented with HEPES (5 mM) was added to pellet that now contained microvesicles and the resuspended microvesicles were transferred to Eppendorf tubes (1.6 ml) in which they were spun at maximum speed for 60 min at 4° C. The supernatant was discarded and PBS supplemented with HEPES was added to the pellet, spun again at maximum speed for 60 min at 4° C. The so obtained pellet was resuspended pellet in a small volume of PBS supplemented with HEPES (usually 100-200 mcl).

Figure 2A:
FIG. 2A is a photograph of an agarose gel with Her2-RNA amplification products of RNA from microvesicles that were isolated from culture supernatants of the selected cell lines.
Figure 2B:
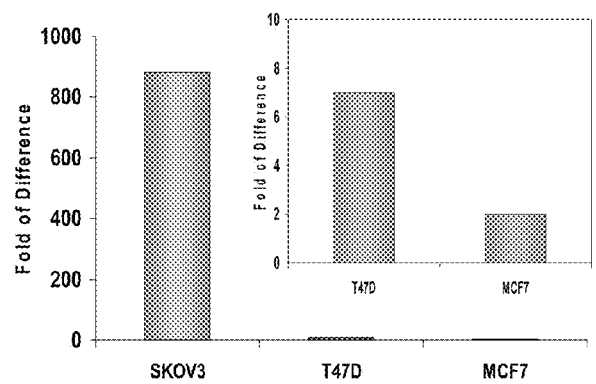
FIG. 2B is a graph depicting the quantitative difference of the amplification products of FIG. 2A.

PCR Analysis: Using the methods described for cells above, total RNA was isolated from the microvesicles, and real time PCR and regular PCR were performed. When using real time PCR, Her-2 was detected only in microvesicles from the SKOV cell culture but not from T47D and MCF cell culture. However, when using regular PCR, Her-2 was detectable on the mRNA level from all three cell cultures by agarose gel electrophoresis as can be seen in FIG. 2A. Not surprisingly, a quantitative analysis of the agarose gel electrophoresis showed that microvesicles from the SKOV cell culture provided the strongest her-2 signal, which was followed by the T47D cell culture, which was in turn followed by the MCF cell culture. A quantitative graph illustrating these results is shown in FIG. 2B. It should therefore be appreciated that cellular expression levels of Her-2 are paralleled by microvesicular Her-2 RNA quantities detected in the culture supernatants of the respective cell lines.

Detection of Her-2 in Microvesicles from Murine Serum of Mice Harboring SKOV Derived Tumors Mice with SKOV-derived Tumors: Athymic nude mide were injected with 3×10$^6$ SKOV3 cells using standard protocol to establish solid tumors in these mice. After three weeks, presence of palpable/measurable tumors was confirmed, and serum was collected from the animals as well as from control mice without tumors (no SKOV injection).

Figure 3A:
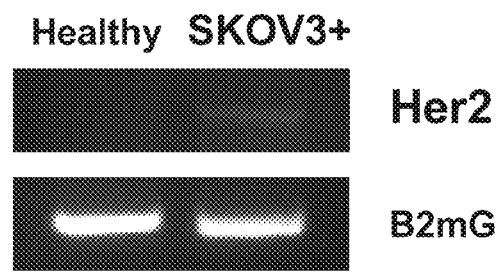
FIG. 3A is a photograph of an agarose gel with Her2-RNA amplification products of RNA from microvesicles that were isolated from murine serum of mice that developed tumors derived from one of the selected cell lines.
Figure 3B:
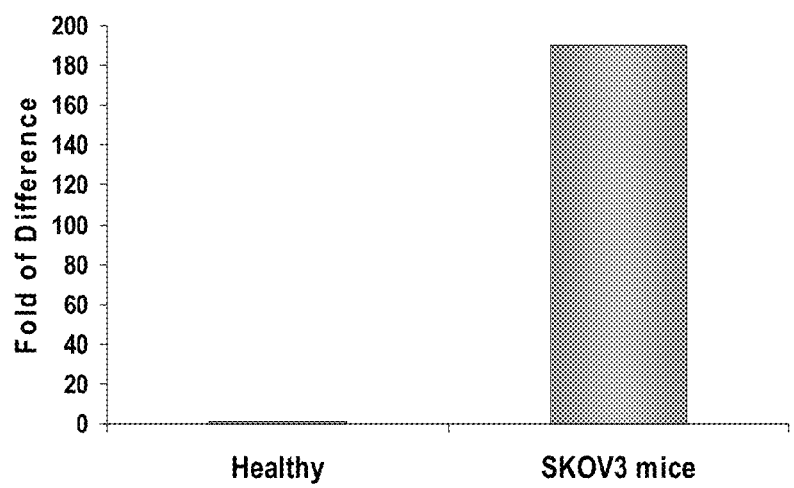
FIG. 3B is a graph depicting the quantitative difference of the amplification products of FIG. 3A.

The microvesicles were isolated from the serum following the general protocol as outlined above. The total RNA obtained from the microvesicles was evaluated for the presence of Her-2 RNA using the PCR protocols as provided above. PCR products were quantified and checked via agarose gel electrophoresis and exemplary results are shown in FIG. 3A (to ensure analysis of equal amounts, control PCR was performed using beta-2-microglobulin as standard). A graphic representation of the Her-2 quantification of corresponding rtPCR is shown in FIG. 3B. Based on these results, it should be appreciated that SKOV-tumor derived microvesicles that were generated in vivo were not only positive for Her-2 RNA, but that such RNA can also be detected from a relatively small blood sample with a high degree of sensitivity and specificity.

Detection of Her-2 in Microvesicles from Human Serum of Patients Diagnosed with Her-2 Positive Breast Cancer To validate the concept of using microvesicles as proxy diagnostic markers for diseased or otherwise distressed cells, blood samples were analyzed from patients diagnosed with Stage I and II breast cancer that was characterized by immunohistochemical assay as Her-2 positive at level 3+.

Figure 4A:
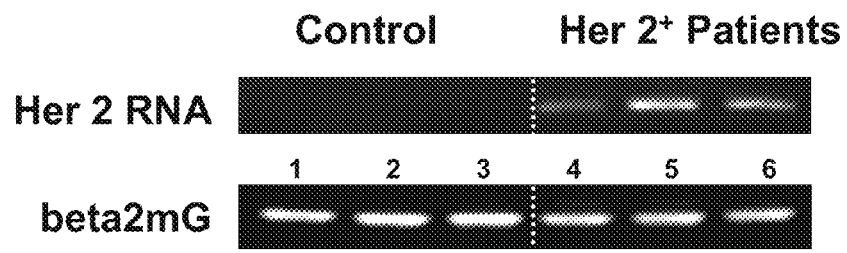
FIG. 4A is a photograph of an agarose gel with Her2-RNA amplification products of RNA from microvesicles that were isolated from human sera of patients with confirmed breast cancer diagnosis.
Figure 4B:
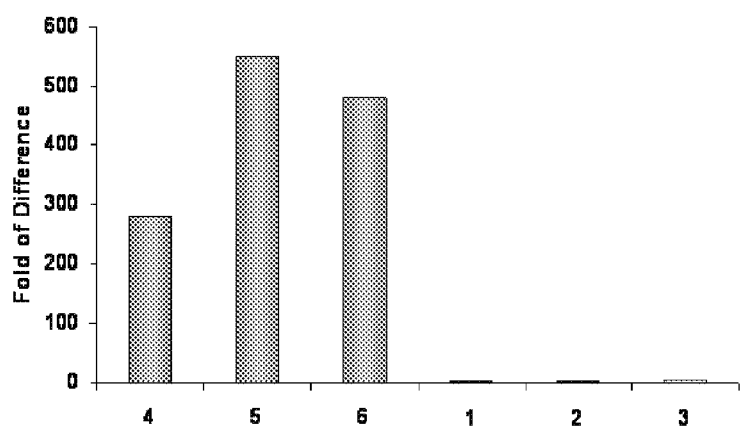
FIG. 4B is a graph depicting the quantitative difference of the amplification products of FIG. 3A.

Microvesicles were isolated from actual patient and control sera following the general protocol as outlined above, and total RNA obtained from the microvesicles was evaluated for the presence of Her-2 RNA using the PCR protocols as provided above. The PCR products were quantified and checked via agarose gel electrophoresis and the results for these experiments are shown in FIG. 4A (to ensure analysis of equal amounts control PCR was again performed using beta-2-microglobulin as standard). Remarkably, none of the control sera from healthy volunteers showed any detectable Her-2 RNA as tested by rtPCR and normal PCR, but all three of the patients with confirmed breast cancer exhibited a significant and strong signal. Moreover, while patients in lane 4 and 6 were staged at Stage I, the patent in lane 5 was diagnosed at Stage II, which correlated with the strongest signal. The corresponding graphic representation of the Her-2 quantification is shown in FIG. 4B. Based on these results, it should be appreciated that microvesicles can act as sensitive proxy diagnostic tools for the cells from which they originate. Still further, it is noted that such analysis can be performed not only the without radiation burden from radiographic analyses, but also in a manner that entirely avoids any biopsies It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A method of isolating and characterizing a first mammalian cellular RNA of a plurality of extracellular microvesicles, the method comprising the steps of:
   providing a sample that includes a plurality of mammalian cells and a plurality of extracellular microvesicles;
   separating the plurality of microvesicles from the plurality of mammalian cells, and detecting the first mammalian cellular RNA from the separated extracellular microvesicles using a step of hybridization or amplification, wherein the detected first mammalian cellular RNA is a known marker of a disease;
   detecting a second mammalian cellular RNA from the sample using a second step of hybridization or amplification; and
   correlating the detected first mammalian cellular RNA with the detected second mammalian cellular RNA to thereby characterize the first mammalian cellular RNA.

2. A method of isolating and characterizing a first mammalian cellular RNA of a plurality of extracellular microvesicles, the method comprising the steps of:
   obtaining from a mammal a sample that comprises a plurality of extracellular microvesicles that include the first mammalian cellular RNA, wherein the sample further comprises a second mammalian cellular RNA;
   detecting the first mammalian cellular RNA from the plurality of extracellular microvesicles using a step of hybridization or amplification, wherein the detected RNA is a known marker of a disease;
   detecting the second mammalian cellular RNA from the sample using a second step of hybridization or amplification; and
   correlating the detected first mammalian cellular RNA with the detected second mammalian cellular RNA to thereby characterize the first mammalian cellular RNA.

3. In a method of isolating a mammalian cellular RNA from a biological fluid, the improvement comprising:
   obtaining from a mammal a biological fluid, wherein the biological fluid comprises a plurality of extracellular microvesicles;
   isolating the plurality of extracellular microvesicles from the biological fluid; and detecting the mammalian cellular RNA from the plurality of extracellular microvesicles using a step of hybridization or amplification, wherein the detected RNA is a known marker of a disease.

4. The method of claim 1 or claim 2 wherein the second mammalian cellular RNA is detected from the extracellular microvesicles using a step of hybridization or amplification.

5. The method of claim 1 or claim 2 wherein the detected first mammalian cellular RNA is a known marker of a neoplastic disease.

6. The method of claim 1 or claim 2 wherein the step of detecting the first mammalian cellular RNA comprises quantifying the first mammalian cellular RNA.

7. The method of claim 1 or claim 2 wherein the step of detecting the second mammalian cellular RNA comprises quantifying the first mammalian cellular RNA.

8. The method of claim 1 or claim 2 wherein the second mammalian cellular RNA is exclusively expressed in a single tissue.

9. The method of claim 1 or claim 2 wherein the step of correlating comprises a quantitative correlation of the first detected mammalian cellular RNA with the detected second mammalian cellular RNA.

10. The method of claim 1 or claim 2 wherein the sample is selected from the group consisting of blood, serum, urine, and a solid tissue.

11. The method of claim 3 wherein the biological fluid is blood, serum, or urine.

12. The method of claim 3 wherein the step of detecting the mammalian cellular RNA is performed using hybridization of the mammalian cellular RNA to a solid phase or by quantitative rtPCR.

13. The method of claim 3 wherein the detected mammalian cellular RNA is a known marker of a neoplastic disease.

* * * * *